US006763698B2

(12) United States Patent
Greenwood

(10) Patent No.: US 6,763,698 B2
(45) Date of Patent: Jul. 20, 2004

(54) SELF CALIBRATING SYSTEM AND TECHNIQUE FOR ULTRASONIC DETERMINATION OF FLUID PROPERTIES

(75) Inventor: Margaret Stautberg Greenwood, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 86 days.

(21) Appl. No.: 10/099,412

(22) Filed: Mar. 15, 2002

(65) Prior Publication Data

US 2003/0172734 A1 Sep. 18, 2003

(51) Int. Cl.[7] .................................. G01N 9/24
(52) U.S. Cl. ................. 73/30.01; 73/32 A; 73/54.41; 73/61.79; 73/64.53; 73/602
(58) Field of Search ............... 73/597–600, 602, 73/30.01, 32 A, 54.01, 54.41, 61.49, 61.79, 64.53

(56) References Cited

U.S. PATENT DOCUMENTS 2,959,054 A 11/1960 Welkowitz
2,966,058 A 12/1960 McSkimin (List continued on next page.)

FOREIGN PATENT DOCUMENTS

DE 19535848 7/1996
EP 0364168 4/1990

OTHER PUBLICATIONS

"On–line Sensor for Density and Viscosity Measurement of a Liquid or Slurry for Process Control in the Food Industry", Greenwood, M., Skorpik, J., Bamberger, J., presented at American Society of Chemical Engineers Conference on Food Engineering '99 Sensors and Controls technical session (T3014).

"An In–Line Ultrasonic Viscometer", Sheen, S.H., Chien, H.T., Raptis, A.C., Review of Progress in Quantitative Nondestructive Evaluation, vol. 14, Plenum Press, New York, 1995, pp. 1151–1158.

Fundamentals of Ultrasonics, Blitz, Jack, Second Edition, New York Plenum Press, London, Butterworth, 1967, pp. 130–134.

"Dynamic Viscosity Measurement", Harrison, G. and Barlow, A., Methods of Experimental Physics, Academic Press, vol. 19, 1981, pp. 137–178.

*Primary Examiner*—Hezron Williams
*Assistant Examiner*—Rose M. Miller
(74) *Attorney, Agent, or Firm*—Woodard, Emhardt, Moriarty, McNett & Henry LLP

(57) ABSTRACT

A system and technique for determining fluid properties includes an ultrasonic transducer 30 on a first surface 42 of a solid member 40. An opposed second surface 44 of the member 40 is in contact with a fluid 25 to be monitored. A longitudinal ultrasonic pulse is delivered through the solid member, and a multiplicity of pulse echoes caused by reflections of the ultrasonic pulse between the solid-fluid interface and the transducer-solid interface are detected and processed by a processing apparatus 22. The apparatus 22 determines the decay rate of the detected echo amplitude as a function of echo number and compares this value to a calibrated decay rate to determine an acoustic property of the fluid. The speed of ultrasound in the fluid is also determined and the fluid density is determined as a function of the speed of ultrasound and the determined acoustic property. When coupled with a shear wave transducer, additional properties corresponding to the fluid viscosity, shear modulus, or shear speed are also determined. Both a fixed in place sensing system and a clamp-on sensing system are disclosed.

45 Claims, 3 Drawing Sheets

U.S. PATENT DOCUMENTS

| | | | |
|---|---|---|---|
| 3,791,200 A | * 2/1974 | Hayre | 73/589 |
| 4,144,517 A | * 3/1979 | Baumoel | 367/93 |
| 4,145,917 A | * 3/1979 | Brazhnikov et al. | 73/64.53 |
| 4,149,139 A | 4/1979 | Kronk | |
| 4,203,324 A | * 5/1980 | Baumoel | 73/290 V |
| 4,320,659 A | 3/1982 | Lynnworth et al. | |
| 4,403,508 A | * 9/1983 | Langlois | 73/589 |
| 4,414,849 A | 11/1983 | Brown et al. | |
| 4,571,693 A | 2/1986 | Birchak et al. | |
| 4,601,292 A | 7/1986 | Fidel et al. | |
| 4,614,115 A | 9/1986 | Pelletier et al. | |
| 4,991,124 A | 2/1991 | Kline | |
| 5,062,299 A | 11/1991 | Davis et al. | |
| 5,365,778 A | 11/1994 | Sheen et al. | |
| 5,456,114 A | * 10/1995 | Liu et al. | 73/597 |
| 5,467,321 A | 11/1995 | Baumoel | |
| 5,473,934 A | * 12/1995 | Cobb | 73/61.49 |
| 5,640,234 A | 6/1997 | Roth et al. | |
| 5,686,661 A | * 11/1997 | Singh et al. | 73/54.41 |
| 5,708,191 A | 1/1998 | Greenwood et al. | |
| 5,886,250 A | 3/1999 | Greenwood et al. | |
| 5,886,262 A | 3/1999 | Sinha | |
| 6,050,141 A | * 4/2000 | Tello et al. | 73/152.56 |
| 6,082,180 A | 7/2000 | Greenwood | |
| 6,082,181 A | 7/2000 | Greenwood | |
| 6,112,254 A | * 8/2000 | Cherek et al. | 710/1 |
| 6,141,625 A | 10/2000 | Smith et al. | |
| 6,227,040 B1 | 5/2001 | Hastings | |
| 6,330,831 B1 | 12/2001 | Lynnworth et al. | |
| 6,575,043 B1 | * 6/2003 | Huang et al. | 73/861.25 |

\* cited by examiner

US 6,763,698 B2

SELF CALIBRATING SYSTEM AND TECHNIQUE FOR ULTRASONIC DETERMINATION OF FLUID PROPERTIES

BACKGROUND

The present invention relates to fluid analysis and more particularly, but not exclusively, relates to the determination of fluid properties by detecting ultrasonic reflections from a solid-fluid interface.

Fluids are encountered in a wide variety of industrial applications, and there is a continual need to determine properties of those fluids. One approach to the determination of fluid properties is based on measuring the reflection of ultrasound from a solid-fluid interface. The relative amount of ultrasound that reflects from a solid-fluid interface, expressed as a reflection coefficient, is a function of properties of the solid and fluid material. Therefore, at least in theory, if the reflection coefficient can be measured and the relevant properties of the solid are known, properties of the fluid can be determined. However, existing techniques for determining fluid properties based on reflections from a solid-fluid interface fail to satisfactorily address all industrial requirements.

For example, operating conditions of ultrasonic transducers and sensors assemblies can change over time. These changes can compromise the accuracy and precision of a measurement, and the adverse effects become particularly problematic when it is desirable to make comparisons between measurements taken at substantially different times. As changes in operating conditions become more significant and unpredictable, it becomes increasingly difficult to accurately compensate for such changes, and comparisons between data taken at different times becomes unreliable.

In addition, metals such as stainless steel and aluminum are common materials for fluid conduits and containers, but their usefulness in an accurate reflection based acoustic sensor is limited. One reason is that metals have a large acoustic impedance relative to the acoustic impedance of typical fluids. This large relative difference reduces the sensitivity of the reflection coefficient to changes in fluid properties. For example, at a stainless steel-water interface, where the acoustic impedance ratio of stainless steel to water is about 30.0, approximately 93.5% of ultrasound is reflected back into the steel from the interface in a normal incidence pulse-echo arrangement. An increase in the density of the fluid by about 6%, results in about 93.1% of the ultrasound being reflected, a difference of only about 0.4%.

Additionally, the speed of sound in metals is relatively high. Accordingly, for a given sound frequency, the wavelength of ultrasound in metals is relatively long. For example, at 2.5 MHz the wavelength of ultrasound is about 0.08 inches in stainless steel, which places significant limits on the cycle length of a 2.5 MHz sound pulse that would avoid echo overlap in a zero degree echo configuration in a thin member.

Accordingly, there is a need further contributions in this area of technology, including but not limited to better systems and techniques for determining fluid properties based on measuring acoustic reflections from an interface.

SUMMARY

One embodiment of the present invention includes a unique technique for fluid analysis. Other embodiments include unique methods, systems, devices, and apparatus for determining fluid properties.

In one embodiment a unique ultrasonic fluid interrogation system is provided including a transducer associated with a first surface of a wall with the fluid in contact with an opposed second surface of the wall. The transducer is operable to deliver an ultrasound pulse into the wall, with the ultrasound pulse reflecting in the wall between the first and second surfaces to provide an ultrasound pulse echo series at the transducer. The system includes means to detect a number of echoes from the echo series and to process the detected echoes to determine the decay rate of the echoes in the series. The decay rate is then compared to a calibrated decay rate to determine an acoustic property of the fluid. In one form, the transducer is clamped on to a pipe or container wall to provide a retrofit sensor device. In other forms, the wall is a metal, such as stainless steel. In still other forms a physical property of the fluid, such as the fluid density, viscosity, shear modulus, and/or shear speed is also determined. In still further forms the wall is thin relative to the size of the transducer face associated with the wall. In still further forms, the ultrasound pulse is a broadband pulse.

In a further embodiment, fluid properties are determined by delivering an ultrasonic pulse through a solid member with a transducer, reflecting the ultrasonic pulse between a solid-fluid interface and the transducer-solid interface a number of times producing a number of ultrasonic pulse echoes at the transducer, detecting the echoes, and determining the decay rate of the echo amplitude as a function of echo number. The decay rate is then compared to a calibrated decay rate to determine an acoustic property of the fluid, such as the acoustic impedance. In further refinements, the speed of ultrasound in the fluid is also determined and the fluid viscosity and/or fluid density is determined as a function of the acoustic property and the speed of ultrasound. In these or still further refinements, the transducer face is selected to be larger than the thickness of the solid member. In still further refinements, the size of the transducer face relative to the thickness of the solid member is selected such that the pathlength for the majority of the detected pulse echoes is less than the near field length of the ultrasonic transducer.

One object of the present invention is to provide a unique technique for fluid characterization.

Another object of the present invention is to provide a unique method, system, device, or apparatus for determining fluid properties capable of utilizing ultrasonic reflections from the metal-fluid interface in a pipe wall.

Another object of the present invention is to provide a unique ultrasonic method, system, device, or apparatus for determining fluid properties that is substantially independent of variations in inputs to the ultrasonic transducer and/or is substantially independent of the amplitude of measured signals.

Another object of the present invention is to provide a unique ultrasonic method, system, device, or apparatus for determining fluid properties capable of including a transducer clamped on to a preexisting pipe or container wall to provide a retrofit sensor.

Further embodiments, forms, features, aspects, benefits, objects, and advantages shall become apparent from the detailed description and figures provided herewith.

DETAILED DESCRIPTION

Figure 1:
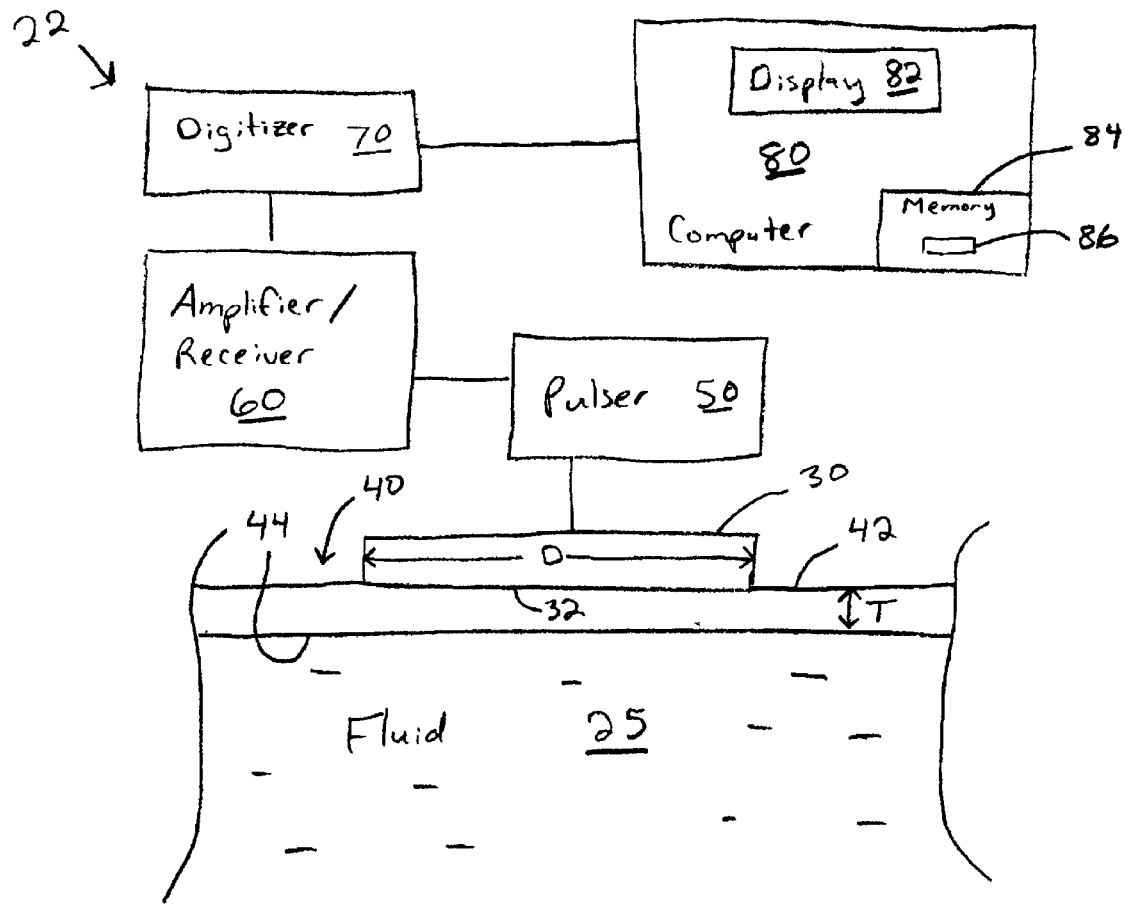
FIG. 1 is a diagrammatic view of system for determining fluid properties.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Turning now to FIG. 1, a system 20 for analyzing a property of fluid 25 is depicted. Fluid 25 can be a gas, liquid, slurry, suspension, paste, emulsion and the like. In preferred forms, fluid 25 is substantially non gasseous and/or includes at least one liquid. In this form, fluid 25 might be, for example, a liquid, slurry, or suspension. In further preferred forms fluid 25 has a viscosity greater than about 0.5 cP and/or a density greater than about 0.3 g/cm$^3$.

Ultrasonic transducer 30 is acoustically coupled to a first surface 42 of a member 40 comprised of a solid material. In one example, transducer 30 is in direct contact with member 40. In other examples, one or more couplants might be used between transducer 30 and member 40, or they may be coupled as would otherwise occur to those skilled in the art. An opposed second surface 44 of member 40 is in contact with the fluid 25. A pulser 22 is electrically coupled to transducer 30 and is operable to deliver input stimulus signal to transducer 30 to cause transducer 30 to emit acoustic energy through solid member 40 and towards fluid 25. Transducer 30 is also operable to produce output signals in response to acoustic energy transmitted from member 40. A processing apparatus 22 including receiver 60, digitizer 70, and computer 80, is coupled to pulser 22 and to transducer 30. Processing apparatus 22 controls delivery of the transducer input signals, receives the output signals from transducer 30, and, as described more fully below, performs calculations to determine properties of fluid 25 as a function of the transducer output signals.

Figure 7:
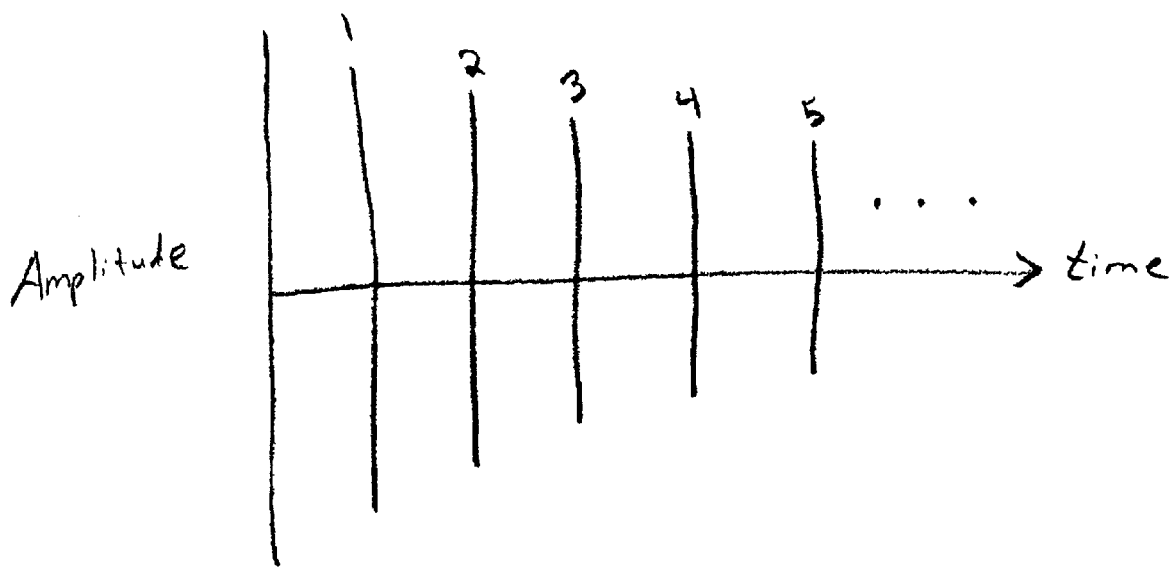
FIG. 7 is an exemplary plot of echo magnitude versus time illustrating echoes 1–5 of a representative diminishing series of echo amplitudes.

In operation, pulser 50 generates and delivers a short duration stimulus to transducer 30. Transducer 30 responds to the stimulus by emitting a longitudinal wave pulse of ultrasound into member 40. This ultrasonic pulse reflects between surfaces 44 and 42 producing a series of pulse echoes at transducer 30. This resulting echo series will be of successively diminishing echo amplitude because each successive echo will have reflected from the solid fluid interface at surface 44 one time more than the previous echo. An exemplary plot of echo magnitude versus time after the initial pulse, illustrating echoes 1–5 of a diminishing series of echoes, is shown in FIG. 7.

Transducer 30 responds to the echoes by producing an output signal proportional to the echo amplitude that is amplified by receiver 60, digitized by digitizer 70 and passed to computer 80. Computer 80 includes programming instructions encoded on fixed and/or removable memory devices 84, 86, respectively, to select a peak echo amplitude for the series echoes and to determine the average decay rate of the peak echo amplitudes with increasing echo number in the echo series. Alternatively, computer 80 can be at least partially hard wired with dedicated memory devices and configured to execute logic according to the present invention. Computer 80 is operatively coupled to display 82 to output selected information about fluid 25 integrated with transducer 30.

Preferably a number of echo amplitudes, for example 5 or more, spanning a range of echo numbers are used in computing the decay rate. In one preferred form, computer 80 is programmed to first compute the fast Fourier transform (FFT) of the digitized signal, converting it from the time domain to the frequency domain and then determine the peak amplitude at a selected frequency, where the frequency is selected to be, for example, the center frequency of transducer 30. In a still further preferred form, the process is repeated for a number of pulses from transducer 30, and the average decay rate of the peak echo amplitudes is determined for each repetition. A rolling average of the resulting set of average decay rates is then determined.

Figure 8:
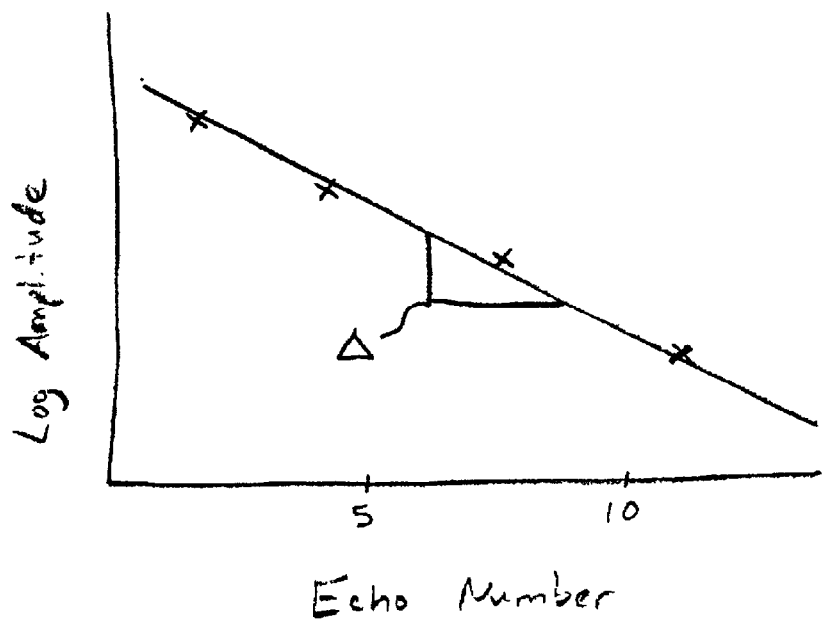
FIG. 8 is an exemplary plot of log echo amplitude versus echo number with a straight line fit to the exemplary data.

The determined average decay rate can be expressed as the slope of the line of the natural log of echo amplitude versus echo number ($\Delta F$). An exemplary plot of log echo amplitude versus echo number with a line fit to the exemplary data is shown in FIG. 8. Utilizing this expression of the average decay rate, computer 80 calculates the reflection coefficient for the fluid-solid interface (RCfluid) according to equation (1)

$$RCfluid/RCcalib = e^{(\Delta F - \Delta C)} \qquad (1)$$

where $\Delta C$ is the slope of the natural log of echo amplitude versus echo number determined by replacing the fluid 25 with a calibration fluid, and RCcalib is the calculated reflection coefficient for the fluid-solid interface when the fluid is the calibration fluid. The values for RCcalib and $\Delta C$ are stored in memory 84 and/or 86, and the value for RCcalib is calculated in advance according to equation (2)

$$RCcalib = (Zcalib - Zsolid)/(Zcalib + Zsolid) \qquad (2)$$

where Zcalib is the acoustic impedance of the calibration fluid and Zsolid is the acoustic impedance of the solid member 40.

From the fluid specific reflection coefficient (RCfluid), computer 80 calculates the acoustic impedance of the fluid (Zfluid) according to equation (3)

$$Zfluid = Zsolid\ (1 - RCfluid)/(1 + RCfluid) \qquad (3)$$

where Zsolid is the acoustic impedance of the solid member 40.

From the acoustic impedance of the fluid (Zfluid), computer 80 calculates a physical property of the fluid. The density of the fluid ($\rho F$) is calculated according to equation (4)

$$\rho F = Zfluid/Vfluid \qquad (4)$$

where Vfluid is the speed of the sound in the fluid. An indication of the fluid density is then produced on display 82.

Figure 2:
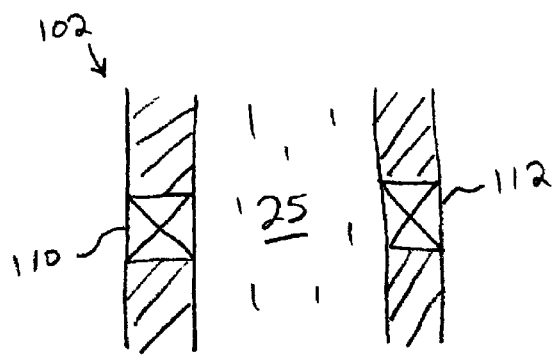
FIG. 2 is a schematic view of a device for performing an ultrasonic time-of-flight measurement on a fluid.
Figure 3:
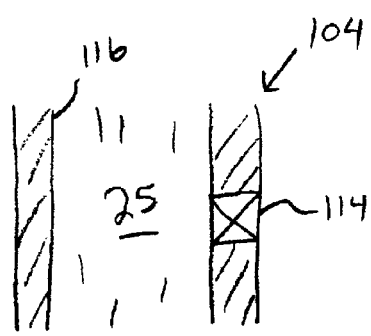
FIG. 3 is a schematic view of another device for performing an ultrasonic time-of-flight measurement on a fluid.
Figure 4:
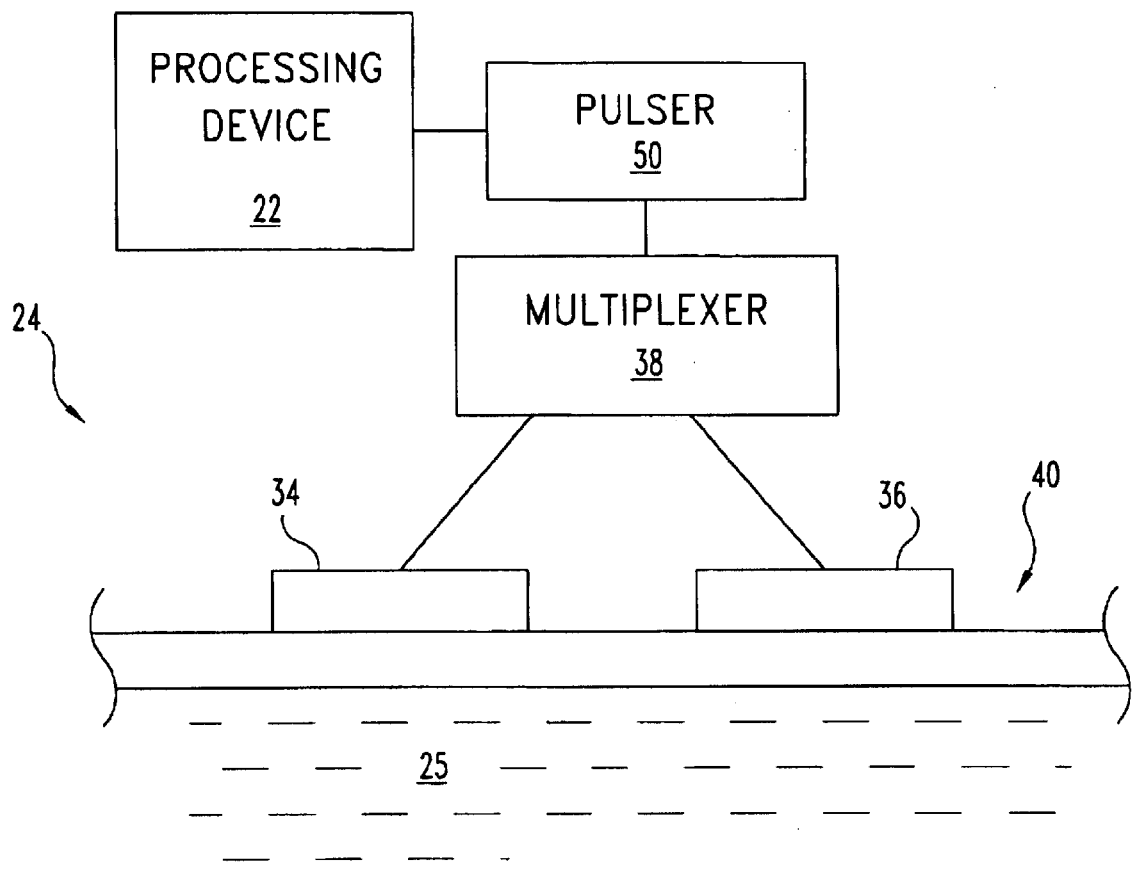
FIG. 4 is a diagrammatic view of a variation of the FIG. 1 system for determining fluid properties.

In a preferred form, the speed of sound (Vfluid) is determined by performance of a time-of-flight measurement on the fluid. A time-of-flight measurement is accomplished by measuring the time it takes an ultrasound pulse to travel a known distance through the fluid 25. The speed of sound (Vfluid) is then determined by dividing the known distance by the determined transit time. FIGS. 2 and 3 schematically illustrate devices 102 and 104 for performing time-of-flight measurements that can form a portion of system 20. In the FIG. 2 embodiment, a pair of transducers 110, 112 are arranged in pitch-catch mode and measure the time it takes sound to travel from transducer 110 to transducer 112. In the FIG. 3 embodiment, a single transducer 114 is arranged relative to a surface 116 in pulse-echo mode for measuring the time it takes sound to travel from transducer 114 to surface 116 and back. Because the ultrasound travels through the fluid in a time-of-flight measurement, it is preferred to use a lower frequency of ultrasound in the time-of-flight measurement than in the echo measurement to minimize attenuation of ultrasound in the fluid during the time-of-flight measurement. In particular forms, the time-of-flight measurement is performed at a frequency below about 1 MHz One variation of system 20 is depicted in FIG. 4. System 24 includes both a shear wave transducer 34 and a longitudinal wave transducer 36. Transducers 34 and 36 are each coupled to pulser 50 and processing apparatus 22 via a multiplexer 38. In this variation, processing apparatus 22 is programmed to simultaneously or sequentially cause shear waves and longitudinal waves to be reflected through member 40. Processing apparatus 22 is programmed to receive the output of longitudinal transducers 34 when longitudinal waves are being reflected through member 40 and to determine fluid density information as described above with respect to system 20. Alternatively, longitudinal wave transducer 34 can be omitted with fluid density determined by any other means known in the art.

Processing apparatus 22 is also programmed to determine one or more additional properties of the fluid utilizing the response of transducer 36 to the reflected shear waves in combination with the determined density information. The response from shear transducer 36 is process as described above with respect to transducer 30 to calculate the acoustic impedance of the fluid according to equations (1)–(3), where the values used in equation (1)–(3) and the determined acoustic impedance (Zfluid) appropriately correspond to values for shear waves.

In one preferred form, the additional properties determined from the shear wave acoustic impedance depend on the properties of the fluid being interrogated. The propagation of a shear waves in liquids is described in J. Blitz, Fundamentals of Ultrasonics, $2^{nd}$ Edition, Plenum Press, New York, 1967, pp.130–134, which is hereby incorporated by reference in its entirety. As described in Blitz, both the viscosity ($\eta$) and the shear modulus (G) are parameters in differential equations involving the rate of change of the shear strain, the pressure, and the pressure time dependence for shear wave propagation. The relaxation time ($\tau$) for liquids is defined as the viscosity ($\eta$) divided by the shear modulus (G). Where the relaxation time is small such that the terms involving G can be ignored, the viscosity of the fluid ($\eta$) is calculated in accordance with equation (5).

$$Zfluid=(\omega \rho_F \eta/2)^{0.5} \quad (5)$$

where $\omega$ is the radial frequency of the shear wave and $\rho_F$ is the determined fluid density. Exemplary small relaxation times for this form include relaxation times less than about $10^{-9}$ and more preferably on the order of about $10^{-12}$. An equivalent formulation for determining fluid viscosity by combining equations (3) and (5) and substituting for Zsolid is given in equation (5a).

$$(\rho_F \eta)^{0.5} = \rho s c_{TS} \left(\frac{2}{\omega}\right)^{0.5} \left(\frac{1 - RCfluid}{1 + RCfluid}\right) \quad (5a)$$

where $\rho s$ is the density of the solid and $c_{TS}$ is the shear wave velocity in the solid.

For fluids 25 where the value of $\omega\tau \gg 1$, shear modulus (G) or the shear velocity in the fluid ($c_{tf}$) can be calculated according to equations (6) and (7).

$$Zfluid=(\rho_F G)^{0.5} \quad (6)$$

$$Zfluid=(\rho_F c_{tf}) \quad (7)$$

Exemplary values for $\omega\tau$ according to this form include values greater than about 3 and more preferably greater than about 11.

In other forms or where these simplifications are not utilized, additional fluid properties can be determined by solving Blitz's differential equations numerically and/or by any means known in the art.

Transducers useful for forming and receiving the ultrasound pulse echo series in practicing the present invention can operate in the range of about 0.5 to 20 MHz, more preferable between about 1 and 10 MHz, and most preferably about 5 MHz. In certain applications of the invention, the thickness T of member 40 will be predetermined, and depending on the wavelength of ultrasound in the member 40, the ratio of thickness T to wavelength could be significant, for example greater than about 0.05. As one example, it is contemplated that member 40 would be the existing wall of a stainless steel pipe or container about 0.15 inches thick. For at least some selected ultrasonic frequencies, the wavelength of ultrasound will be significant relative to the wall thickness.

Where the length of the pulse in the member 40 is a concern, a broadband ultrasound pulse can be used. Pulser 50 inputs a square wave or spike input to transducer 30, where the non-sinusoidal input has a duration less than the time it takes the transducer to perform a half cycle at the transducer center frequency (give by the inverse of the frequency of the transducer). The transducer 30 responds to this short input stimulus by emitting an ultrasonic pulse into member 40 of short duration, for example on the order of about 3–4 wavelengths in length. In this manner, the length of the ultrasound pulse in member 40 can be minimized and the echoes detected by transducer 30 can be readily resolved, because the potential for overlap is typically reduced.

In another form of the invention, because of the materials desired for solid member 40 and fluid 25, the acoustic impedance ratio Zsolid/Zfluid will be significant, for example, greater than about 5 or 10. In this form, the ultrasound pulse is preferably detected as it undergoes a large number of reflections between surfaces 42 and 44 of member 40, for example more than about 10 reflections, preferably about 15–20 reflections. The multiple reflections serve to amplify the effect of small changes in properties of fluid 25. This amplification occurs because the amplitude of the pulse is diminished in accordance with the reflection coefficient (RCfluid) with each successive reflection with surface 44. Also, because the higher echoes undergo more reflections with surface 44 and because the reflection coefficient (RCfluid) is a function of fluid properties, the effect of changes in these fluid properties are more pronounced in the higher echo numbers. Consequently, in one form of the invention, it is preferred that at least some of the higher number echoes are used in computing the decay rate.

In further forms of the invention, where reduction of the adverse effects of divergence and/or attenuation is of concern, selection of transducer 30 and member 40 dimensions and properties can be of particular interest. For example, the near field can be considered the region immediately in front of an ultrasonic transducer where the sound beam is does not diverge and signal loss is at a minimum. The near field length (Nf) for an ultrasonic transducer can be approximated by equation (8)

$$Nf=0.25D^2/lambda \quad (8)$$

where lambda is the wavelength of the ultrasound in the medium (equal to local speed of sound divided by the frequency) and D is the largest dimension of the transducer face 32 associated with the member 40. For circular transducers, D will be the diameter of the face 32 whereas for rectangular transducers D will be the larger length dimension of the rectangle. In one form of the invention, the near field of the transducer 30 is selected to encompass one or more of the reflections used to calculate the decay rate. In a preferred form, a plurality of the echoes used to calculate the decay rate are within the near field length estimated by equation (8). In a further preferred form, the majority of the echoes used to calculate the decay rate are within this length. Most preferably, substantially all of the echoes are within this length.

From an examination of equation (8) one possibility for increasing the near field length is to increase the frequency of the ultrasound. However, there is a practical limit to the effectiveness of this approach, at least because losses due to attenuation of the ultrasound generally increase with increasing frequency. The near field length is therefore preferably maintained at a desired relative length by adjusting the ratio of the size of transducer size D to thickness T. Increasing the transducer size D increases the near field length whereas decreasing T decreases the pathlength of the echoes, allowing more echoes to be detected inside a given near field length. It is to be understood that the pathlength for each echo is the distance the pulse travels for each reflection (2T) times the echo number (the first echo has a pathlength of 2T, the second 4T, the third 6T, etc.). While any ratio can be utilized as would occur to those of skill in the art, in one form of the invention the ratio of D/T is preferably greater than about one. In other forms, the ratio D/T is about 2 or above.

An advantage is realized by using the decay rate of the echo amplitudes (represented by the two slopes $\Delta F$ and $\Delta C$) in determining fluid properties. It has been found that, unlike the absolute magnitude of individual echo amplitudes, the slope of echo amplitude versus echo number is substantially independent of characteristics of the ultrasound pulse used to create the echoes. This independence was confirmed experimentally utilizing a 1 inch diameter longitudinal transducer in contact with a 0.25 inch thick stainless steel plate. The transducer operated at 5 MHz and the opposed surface of the plate was in contact with water.

In one set of experiments, the width of a −300 volt square wave input to the transducer was varied. It was found that, while the absolute value of the $6^{th}$ echo amplitude changed by about 21% when the width of the voltage input was changed from 102 nanoseconds to 68 nanoseconds, the slope of the natural log of the FFT amplitude versus echo number changed by less than 0.1%.

In a second set of experiments the voltage of a 100 nanosecond square wave input was changed from −300 volts to −50 volts and the slopes of the amplitude versus echo number log plots were determined. While the magnitude of the voltage input was decreased by a factor of six, the calculated slope of the log of amplitude versus echo number changed by less than 2%.

In one application of the invention, the transducer 30 and solid member 40 are provided as a spool piece that is fixed in place in a pipeline. In other applications of the present invention, preexisting pipe or container walls as utilized as member 40, and transducer 30 is configured as a clamp-on sensor that can be retrofit to existing equipment and/or readily moved from one pipeline or container to the next. In these latter applications, where preexisting walls provide member 40, the use of the slope of the log of echo amplitude versus echo number is particularly advantageous.

Figure 5:
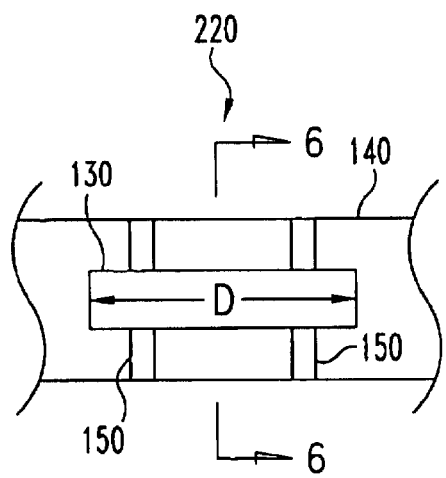
FIG. 5 is a side view of a clamp on sensor attached to a pipeline.
Figure 6:
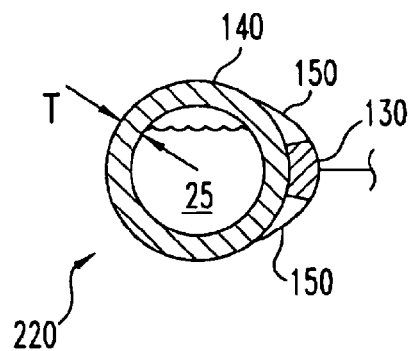
FIG. 6 is a sectional view of the FIG. 5 sensor.

Turning now to FIG. 5, an exemplary clamp on sensor 220 for use on a pipeline is illustrated. Sensor 220 includes an ultrasonic transducer 130 which is used in place of transducer 30 in system 20. Transducer 130 is curved to correspond to the outer diameter of pipe 140, and transducer 130 is held to the outside surface of a pipe 140 with clamps 150 that extend around pipe. Transducer 130 is generally rectangular with its longer dimension D oriented parallel to the flow direction of the pipe 140. This longer length D is preferably greater than the pipe wall thickness T for the reasons described above. As one example, a curved rectangular transducer 0.4 inches by 1 inch could be chosen for a stainless steel pipe with an outside diameter of 2.375 inches and a wall thickness of 0.15 inches. An acoustic couplant, not shown, is optionally provided between transducer 130 and pipe 140. It is to be understood that the strength of any particular signal from transducer 130 might depend on, for example, the pressure exerted by clamps 150, which in turn could depend on additional factors, such as the care with which transducer 130 is attached to pipe 140. However, the slope of the log of echo amplitude versus echo number would be relatively independent of variables such as connection pressure, leading to increased accuracy of the device.

In use, clamp on sensor 220 can be calibrated with any fluid present in pipe 140. If the pipe is empty, air can be the calibration fluid. If the pipeline is conveying a process fluid, the process fluid can be the calibration fluid. Subsequent changes in the process fluid can then be quantitatively or qualitatively determined according to the present invention.

It is to be understood that, while in a retrofit system such as system 220, the existing material of the pipe or container wall dictates the choice of solid material used, a wide variety of materials can serve as the member 40 as would occur to those of skill in the art. Exemplary materials for solid member 40 include aluminum, stainless steel, fused quartz, and plastics. Preferably member 40 is non-porous is does not absorb fluid 25. In particular applications, such as food processing and the transport of toxic material, stainless steel or other non-corrosive materials are preferred materials for solid member 40.

In a further variation, data transmission between computer 80 and transducer 30 can be achieved wirelessly by provision of appropriate wireless communication devices.

It is also to be understood that another embodiment of the present invention is a unique technique to determine fluid properties wherein an ultrasonic transducer 30 is provided on a surface 42 of a solid member 40 having an opposed second surface 44 in contact with the fluid 25. This technique can include delivering an ultrasonic pulse through the solid member, detecting a multiplicity of pulse echoes caused by reflections of the ultrasonic pulse between the solid-fluid interface and the transducer-solid interface, and determining the decay rate of the detected echo amplitude as a function of echo number. The determined decay rate is compared to a calibrated decay rate to determine an acoustic property of the fluid. In one form, the speed of ultrasound in the solid is also determined and the fluid viscosity and/or the fluid density is determined as a function of the speed of ultrasound and the determined acoustic property.

While the invention has been illustrated and described in detail in the drawings and foregoing description, the same is to be considered illustrative and not restrictive in character, it being understood that only the preferred embodiment has been shown and described and that all changes, equivalents, and modifications that come within the scope of the inventions described herein or defined by the following claims are desired to be protected. Any experiments, experimental examples, or experimental results provided herein are intended to be illustrative of the present invention and should not be construed to limit or restrict the invention scope. Further, any theory, mechanism of operation, proof, or finding stated herein is meant to further enhance understanding of the present invention and is not intended to limit

What is claimed is:

1. A method for determining a fluid property comprising:
   delivering an ultrasound pulse to a member with a transducer, the member being comprised of a solid material and including a first surface opposite a second surface, the first surface being coupled to the transducer and the second surface being in contact with a fluid, the ultrasound pulse reflecting between the first surface and the second surface to provide an ultrasound pulse echo series;
   detecting a multiplicity of the ultrasound pulse echoes of the echo series with the transducer;
   determining a first value from the multiplicity of the ultrasound pulse echoes, the first value corresponding to an average decay rate of the multiplicity of the ultrasound pulse echoes;
   determining a second value corresponding to an acoustic property of the fluid from the first value and an established calibration value;
   determining a third value corresponding to speed of ultrasound in the fluid; and
   determining a physical property of the fluid as a function of the second and third values.

2. The method of claim 1 wherein the transducer produces the ultrasonic pulse in response to a first voltage input from a pulser and wherein the second value is determined without correcting the second value by more than about 2% for any difference in the first voltage input from a second voltage input to a transducer used in selecting the established calibration value.

3. The method of claim 2 wherein the first voltage input to the transducer is non-sinusoidal and has a duration less than a half cycle at the center frequency of the transducer.

4. The method of claim 1 wherein the transducer has a face associated with the first surface and the distance between the first surface and the second surface of the member is less than the largest dimension of the transducer face.

5. The method of claim 1 further comprising:
   identifying a wall of a fluid conduit or container containing the fluid to provide the member; and
   coupling the transducer to a portion of the identified wall to provide a retrofit sensing apparatus.

6. The method of claim 5 wherein the wall is stainless steel.

7. The method of claim 1 wherein the ultrasonic pulse is a longitudinal wave and the physical property is fluid density.

8. The method of claim 1 wherein the ultrasonic pulse is a shear wave and the physical property is selected from the group consisting of viscosity, shear modulus, and shear speed.

9. The method of claim 1 wherein an ultrasonic shear wave transducer and an ultrasonic longitudinal wave transducer are each provided and wherein fluid density and a property selected from the group consisting of viscosity, shear modulus, and shear speed are determined.

10. The method of claim 1 wherein the third value is determined by performing a measurement on the fluid.

11. The method of claim 10 wherein the third value is determined by performing a time-of-flight measurement at a frequency below the operational frequency of the transducer.

12. The method of claim 1 wherein the multiplicity of the ultrasound pulse echoes are non-sequential echoes from the echo series.

13. A method for determining a fluid property comprising:
   providing a wall having opposed first and second surfaces, an ultrasonic transducer in association with the first surface, and a fluid in contact the second surface;
   wherein the transducer has a face associated with the first surface and the distance between the first and second surfaces of the wall is less than the largest dimension of the transducer face;
   delivering a pulse of ultrasound to the wall with the transducer, wherein the ultrasound pulse reflects between the first and second surfaces to provide an ultrasound pulse echo series;
   detecting a plurality of the ultrasound pulse echoes of the echo series with the transducer;
   determining a first value from the plurality of the ultrasound pulse echoes, the first value corresponding to an average decay rate of the plurality of the ultrasound pulse echoes; and
   determining a second value corresponding to an acoustic property of the fluid from the first value and an established calibration value.

14. The method of claim further comprising:
   determining a third value corresponding to speed of ultrasound in the fluid; and
   determining a physical property of the fluid as a function of the second and third values.

15. The method of claim wherein the transducer produces the ultrasonic pulse in response to a first voltage input from a pulser and wherein the second value is determined without correcting the second value by more than about 2% for any difference in the first voltage input from a second voltage input to a transducer used in selecting the established calibration value.

16. The method of claim 13 further comprising:
   identifying a wall of a fluid conduit or container containing the fluid to provide the member; and
   coupling the transducer to a portion of the identified wall to provide a retrofit sensing apparatus.

17. The method of claim 13 wherein the wall is stainless steel.

18. The method of claim 13 wherein an ultrasonic shear wave transducer and an ultrasonic longitudinal wave transducer are each provided and wherein the fluid density and a property selected from the group consisting of viscosity, shear modulus, and shear speed are determined.

19. The method of claim 13 wherein the third value is determined by performing a time-of-flight measurement at a frequency below the operational frequency of the transducer.

20. A method for determining a fluid properly comprising:
   providing a fluid in contact with an inner surface of a wall;
   providing an ultrasonic transducer in association with an opposed surface of the wall;
   delivering a pulse of ultrasound to the wall with the transducer by providing a non-sinusoidal stimulus to the transducer, wherein the ultrasound pulse reflects between the inner and opposed surfaces to provide an ultrasound pulse echo series at the transducer
   detecting a plurality of the ultrasound pulse echoes of the echo series with the transducer;
   determining a first value from the plurality of the ultrasound pulse echoes corresponding to a decay rate of the plurality of the ultrasound pulse echoes by selecting a peak echo amplitude at a predetermined frequency for each of the detected echoes and determining a value corresponding to the decay rate of the selected peak echo amplitudes as a function of echo number;

determining a second value corresponding to an acoustic property of the fluid from the first value and a predetermined calibration value;

determining a third value corresponding to speed of ultrasound in the fluid; and determining a physical property of the fluid as a function of the second and third values.

21. The method of claim 20 wherein the transducer has a face associated with the second surface of the wall and the distance between the inner surface and the opposed surface is less than the largest dimension of the transducer face.

22. The method of claim 20 wherein the majority of the detected pulse echoes used to determine the first value have a pathlength in the member less than about 0.25 $D^2$/lambda, where D is the maximum length dimension of the transducer face associated with the member and lambda is the average wavelength of the ultrasound in the wall.

23. The method of claim 20 wherein the wall is metal.

24. The method of claim 20 wherein providing the transducer in association with the wall includes associating the transducer with the wall of an existing fluid conduit or container.

25. An system comprising:
a member comprising solid material having opposed first and second surfaces with the second surface adapted to contact a fluid,
a first ultrasonic transducer in association with the first surface of the member,
a pulser coupled to the transducer; and
a processing apparatus coupled to the transducer;
wherein the pulser is operable to cause the first transducer to deliver a pulse of ultrasound to the member for reflection between the first and second surfaces a predetermined number of times to produce an ultrasound pulse echo series at the transducer;
wherein the processing apparatus is operable to receive signals representing the response of the first transducer to the echoes of the echo series; and
wherein the processing apparatus is operable to determine:
a first value corresponding to an average decay rate of the pulse echoes of the echo series;
a second value corresponding to an acoustic property of the fluid from the first value and a predetermined calibration value;
a third value corresponding to speed of ultrasound in the fluid; and a physical property of the fluid as a function of the second and third values.

26. The system of claim 25 wherein the transducer has a face associated with the first surface and the distance between the first and second surfaces of the solid member is less than the largest dimension of the transducer face.

27. The system of claim 25 further comprising at least a second transducer for determining the speed of ultrasound in the fluid by performing a time-of-flight measurement.

28. The system of claim 27 wherein the second transducer operates at a lower frequency than the first transducer.

29. The system of claim 25 further comprising a fluid in contact with the second surface of the solid member.

30. The system of claim 25 wherein the pulser is operable to deliver a non-sinusoidal impulse to the transducer to cause the transducer to deliver a pulse of ultrasound to the member.

31. The system of claim 25 wherein the physical property is density and the processing apparatus is operable to determine a second property selected from the group consisting of viscosity, shear modulus, and shear speed from the determined fluid density and output signals from a second ultrasonic transducer.

32. The system of claim 31 wherein the first transducer is a longitudinal wave transducer and the second transducer is a shear wave transducer.

33. The system of claim 32 wherein the first and second transducers are each coupled to the member comprising solid material.

34. A method for determining a fluid property comprising:
delivering an ultrasound pulse to a member with a transducer, the member being comprised of a solid material and having a first surface in contact with a fluid and a second surface coupled to the transducer, wherein the surfaces are oriented to produce an ultrasound pulse echo series at the transducer;
detecting a plurality of the ultrasound pulse echoes of the echo series with the transducer;
fitting a curve to at least three data points to determine a first value, the first value corresponding to a decay rate of the plurality of the ultrasound pulse echoes;
determining a second value corresponding to an acoustic property of the fluid from the first value and an established calibration value;
determining a third value corresponding to speed of ultrasound in the fluid; and
determining a physical property of the fluid as function of the second and third values.

35. The method of claim 34 wherein the ultrasonic pulse is a shear wave and the physical property is selected from the group consisting of viscosity, shear modulus, and shear speed.

36. The method of claim 34 wherein an ultrasonic shear wave transducer and an ultrasonic longitudinal wave transducer are each provided and wherein fluid density and a property selected from the group consisting of viscosity, shear modulus, and shear speed are determined.

37. The method of claim 34 wherein the majority of the multiplicity of ultrasound pulse echoes used to determine the first value have a pathlength in the member less than about 0.25 $D^2$/lambda, where D is the maximum length dimension of the transducer face associated with the member and lambda is the average wavelength of the ultrasound pulse in the member.

38. The method of claim 34 wherein the first value is determined by selecting a peak echo amplitude at the same frequency for each of the detected echoes and determining a value corresponding to the average decay rate of the selected peak echo amplitudes for each of the ultrasound pulse echoes as a function of echo number.

39. A method for determining a fluid property comprising:
delivering an ultrasound pulse to a member with a transducer, the member being comprised of a solid material and including a first surface opposite a second surface, the first surface being coupled to the transducer and the second surface being in contact with a fluid, the ultrasound pulse reflecting between the first surface and the second surface to provide an ultrasound pulse echo series;
detecting a multiplicity of the ultrasound pulse echoes of the echo series with the transducer;
determining a first value froth the multiplicity of the ultrasound pulse echoes, the first value corresponding to a decay rate of the multiplicity of the ultrasound pulse echoes;

determining a second value corresponding to an acoustic property of the fluid from the first value and an established calibration value;

determining a third value corresponding to speed of ultrasound in the fluid; and determining a physical property of the fluid as a function of the second and third values;

wherein the majority of the multiplicity of ultrasound pulse echoes used to determine the first value have a pathlength in the member less than about 0.25 $D^2$/lambda, where D is the maximum length dimension of the transducer face associated with the member and lambda is the average wavelength of the ultrasound pulse in the member.

40. A method for determining a fluid property comprising:

delivering an ultrasound pulse to a member with a transducer, the member being comprised of a solid material and including a first surface apposite a second surface, the first surface being coupled to the transducer and the second surface being in contact with a fluid, the ultrasound pulse reflecting between the first surface and the second surface to provide an ultrasound pulse echo series;

detecting a multiplicity of the ultrasound pulse echoes of the echo series with the transducer;

determining a first value from the multiplicity of the ultrasound pulse echoes, the first value corresponding to a decay rate of the multiplicity of the ultrasound pulse echoes;

determining a second value corresponding to an acoustic property of the fluid from the first value and an established calibration value;

determining a third value corresponding to speed of ultrasound in the fluid; and determining a physical property of the fluid as a function of the second and third values;

wherein the transducer produces the ultrasonic pulse in response to a non-sinusoidal voltage input from a pulsar and wherein the first value is determined by selecting a peak echo amplitude at a predetermined frequency for each of the detected echoes and determining a value corresponding to the average decay rate of the selected peak echo amplitude for each of the multiplicity of ultrasound pulse echoes as a function of echo number.

41. The method of claim 40 wherein the transducer produces an output signal in response to the detecting and the transducer output signal is digitized and transformed from time domains to frequency domain prior to selection of the peak echo amplitude for each of the multiplicity of ultrasound pulse echoes.

42. The method of claim 41 wherein at least five of the multiplicity of ultrasound pulse echoes are detected during the detecting.

43. A method for determining a fluid property comprising:

providing a wall having opposed first and second surfaces, an ultrasonic transducer in association with the first surface, and a fluid in contact the second surface;

wherein the transducer has a face associated with the first surface and the distance between the first and second surfaces of the wall is less than the largest dimension of the transducer face;

delivering a pulse of ultrasound to the wall with the transducer, wherein the ultrasound pulse reflects between the first and second surfaces to provide an ultrasound pulse echo series;

detecting a plurality of the ultrasound pulse echoes of the echo series with the transducer;

determining a first value from the plurality of the ultrasound pulse echoes, the first value corresponding to a decay rate of the plurality of the ultrasound pulse echoes; and determining a second value corresponding to an acoustic property of the fluid from the first value and an established calibration value;

wherein the first value is determined by selecting a peak echo amplitude at a predetermined frequency for each of the detected echoes and determining a value corresponding to the average decay rate of the selected peak echo amplitudes for each of the ultrasound pulse echoes as a function of echo number.

44. The method of claim 43 wherein the transducer produces an output signal in response to the detecting and the transducer output signal is digitized and transformed from time domain to frequency domain prior to selection of the peak echo amplitudes for each of the ultrasound pulse echoes.

45. A method for determining a fluid property comprising:

providing a wall having opposed first and second surfaces, an ultrasonic transducer in association with the first surface, and a fluid in contact the second surface;

wherein the transducer has a face associated with the first surface and the distance between the first and second surfaces of the wall is less than the largest dimension of the transducer face;

delivering a pulse of ultrasound to the wall with the transducer, wherein the ultrasound pulse reflects between the first and second surfaces to provide an ultrasound pulse echo series;

detecting a plurality of the ultrasound pulse echoes of the echo series with the transducer;

determining a first value from the plurality of the ultrasound pulse echoes, the first value corresponding to a decay rate of the plurality of the ultrasound pulse echoes; and determining a second value corresponding to an acoustic property of the fluid from the first value and an established calibration value;

wherein the majority of the detected pulse echoes used to determine the first value have a pathlength in the wall less than about 0.25 $D^2$/lambda, where D is the maximum length dimension of the transducer face associated with the member and lambda is the average wavelength of the ultrasound in the member.

* * * * *

UNITED STATES PATENT AND TRADEMARK OFFICE
CERTIFICATE OF CORRECTION

PATENT NO. : 6,763,698 B2  Page 1 of 1
APPLICATION NO. : 10/099412
DATED : July 20, 2004
INVENTOR(S) : Margaret S. Greenwood It is certified that error appears in the above-identified patent and that said Letters Patent is hereby corrected as shown below:

Column 10, line 27, "The method of claim further comprising:" should read -- The method of claim 13 further comprising: --

Column 10, line 32, "The method of claim wherein" should read --The method of claim 13 wherein --

Signed and Sealed this

Eighteenth Day of December, 2007

JON W. DUDAS
*Director of the United States Patent and Trademark Office*